(12) United States Patent
Sutherland et al.

(10) Patent No.: US 10,751,182 B2
(45) Date of Patent: Aug. 25, 2020

(54) SYSTEM AND METHOD FOR RESHAPING RIGHT HEART

(71) Applicant: Edwards Lifesciences Corporation, Irvine, CA (US)

(72) Inventors: Michael Sutherland, Pelham, NH (US); Steven Cahalane, Pelham, NH (US); Morgan House, Newfields, NH (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/393,867

(22) Filed: Dec. 29, 2016

(65) Prior Publication Data

US 2017/0189034 A1 Jul. 6, 2017

Related U.S. Application Data

(60) Provisional application No. 62/272,882, filed on Dec. 30, 2015.

(51) Int. Cl.
*A61F 2/24* (2006.01)
*A61M 25/10* (2013.01)
*A61B 17/12* (2006.01)

(52) U.S. Cl.
CPC ...... *A61F 2/2481* (2013.01); *A61B 17/12136* (2013.01); *A61F 2002/2484* (2013.01);
(Continued)

(58) Field of Classification Search
CPC .... A61F 2/2481; A61F 2/2478; A61F 2/2487; A61F 2/2493; A61F 2230/001; A61M 2025/1072; A61M 2025/105; A61M 2025/1043; A61M 2025/1054; A61M 2025/1059
See application file for complete search history.

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

CN 102869318 1/2013
EP 1034753 A1 9/2019
(Continued)

OTHER PUBLICATIONS

US 6,460,370 B1, 06/2013, Zakay (withdrawn)
(Continued)

*Primary Examiner* — Sarah A Simpson
(74) *Attorney, Agent, or Firm* — Thomas C. Richardson

(57) ABSTRACT

The present teachings provide devices and methods of reshaping the right heart and reducing tricuspid valve regurgitation. Specifically, one aspect of the present teachings provides an inflatable device to be deployed in the space between the sternum and the right heart. An injectable medium is injected to the cavity of the device. Once the device is filled, the device is detached from the delivery system, and released inside the body. The inflated device exerts pressure to the right heart, changes the shape of the tricuspid annulus, and allows a better coaptation of the tricuspid leaflets.

7 Claims, 6 Drawing Sheets

(52) U.S. Cl.
CPC . *A61F 2230/001* (2013.01); *A61F 2250/0003* (2013.01); *A61M 2025/1054* (2013.01)

(56) References Cited

U.S. PATENT DOCUMENTS

| | | | |
|---|---|---|---|
| 3,840,018 A | 10/1974 | Heifetz | |
| 3,881,366 A | 5/1975 | Bradley et al. | |
| 3,898,701 A | 8/1975 | La Russa | |
| 4,042,979 A | 8/1977 | Angell | |
| 4,118,805 A | 10/1978 | Reimels | |
| 4,214,349 A | 7/1980 | Munch | |
| 4,261,342 A | 4/1981 | Aranguren Duo | |
| 4,290,151 A | 9/1981 | Massana | |
| 4,434,828 A | 3/1984 | Trincia | |
| 4,473,928 A | 10/1984 | Johnson | |
| 4,602,911 A | 7/1986 | Ahmadi et al. | |
| 4,625,727 A | 12/1986 | Leiboff | |
| 4,712,549 A | 12/1987 | Peters et al. | |
| 4,778,468 A | 10/1988 | Hunt et al. | |
| 4,819,637 A * | 4/1989 | Dormandy, Jr. ............... A61B 17/12113 137/846 | |
| 4,917,698 A | 4/1990 | Carpentier et al. | |
| 4,961,738 A | 10/1990 | Mackin | |
| 5,041,090 A * | 8/1991 | Scheglov ......... A61B 17/12022 604/101.02 | |
| 5,042,707 A | 8/1991 | Taheri | |
| 5,061,277 A | 10/1991 | Carpentier et al. | |
| 5,064,431 A | 11/1991 | Gilbertson et al. | |
| 5,104,407 A | 4/1992 | Lam et al. | |
| 5,108,420 A | 4/1992 | Marks | |
| 5,201,880 A | 4/1993 | Wright et al. | |
| 5,258,008 A | 11/1993 | Wilk | |
| 5,300,034 A | 4/1994 | Behnke et al. | |
| 5,325,845 A | 7/1994 | Adair | |
| 5,332,402 A | 7/1994 | Teitelbaum | |
| 5,346,498 A | 9/1994 | Greelis et al. | |
| 5,364,408 A | 11/1994 | Gordon | |
| 5,383,852 A | 1/1995 | Stevens-Wright | |
| 5,449,368 A | 9/1995 | Kuzmak | |
| 5,450,860 A | 9/1995 | O'Connor | |
| 5,464,404 A | 11/1995 | Abela et al. | |
| 5,474,518 A | 12/1995 | Ferrer Velazquez | |
| 5,477,856 A | 12/1995 | Lundquist | |
| 5,593,424 A | 1/1997 | Northrup, III | |
| 5,601,572 A | 2/1997 | Middleman et al. | |
| 5,626,609 A | 5/1997 | Zvenyatsky et al. | |
| 5,634,936 A * | 6/1997 | Linden ............... A61B 17/0057 604/60 | |
| 5,643,317 A | 7/1997 | Pavcnik et al. | |
| 5,669,919 A | 9/1997 | Sanders et al. | |
| 5,676,653 A | 10/1997 | Taylor et al. | |
| 5,683,402 A | 11/1997 | Cosgrove et al. | |
| 5,702,397 A | 12/1997 | Goble et al. | |
| 5,702,398 A | 12/1997 | Tarabishy | |
| 5,709,695 A | 1/1998 | Northrup, III | |
| 5,716,370 A | 2/1998 | Williamson, IV et al. | |
| 5,716,397 A | 2/1998 | Myers | |
| 5,728,116 A | 3/1998 | Rosenman | |
| 5,730,150 A | 3/1998 | Peppel et al. | |
| 5,733,331 A | 3/1998 | Peredo | |
| 5,749,371 A | 5/1998 | Zadini et al. | |
| 5,782,844 A | 7/1998 | Yoon et al. | |
| 5,810,746 A | 9/1998 | Goldstein et al. | |
| 5,810,882 A | 9/1998 | Bolduc et al. | |
| 5,824,066 A | 10/1998 | Gross | |
| 5,830,221 A | 11/1998 | Stein et al. | |
| 5,843,120 A | 12/1998 | Israel et al. | |
| 5,855,614 A | 1/1999 | Stevens et al. | |
| 5,876,373 A | 3/1999 | Giba et al. | |
| 5,935,098 A | 8/1999 | Blaisdell et al. | |
| 5,957,953 A | 9/1999 | DiPoto et al. | |
| 5,961,440 A | 10/1999 | Schweich, Jr. et al. | |
| 5,961,539 A | 10/1999 | Northrup, III et al. | |
| 5,984,959 A | 11/1999 | Robertson et al. | |
| 6,042,554 A | 3/2000 | Rosenman et al. | |
| 6,045,497 A | 4/2000 | Schweich, Jr. et al. | |
| 6,048,351 A | 4/2000 | Gordon | |
| 6,050,936 A | 4/2000 | Schweich, Jr. et al. | |
| 6,059,715 A | 5/2000 | Schweich, Jr. et al. | |
| 6,074,341 A | 6/2000 | Anderson et al. | |
| 6,074,401 A | 6/2000 | Gardiner et al. | |
| 6,074,417 A | 6/2000 | Peredo | |
| 6,086,582 A | 7/2000 | Altman et al. | |
| 6,102,945 A | 8/2000 | Campbell | |
| 6,106,550 A | 8/2000 | Magovern et al. | |
| 6,110,200 A | 8/2000 | Hinnenkamp | |
| 6,132,390 A | 10/2000 | Cookston et al. | |
| 6,143,024 A | 11/2000 | Campbell et al. | |
| 6,159,240 A | 12/2000 | Sparer et al. | |
| 6,165,119 A | 12/2000 | Schweich, Jr. et al. | |
| 6,174,332 B1 | 1/2001 | Loch et al. | |
| 6,183,411 B1 | 2/2001 | Mortier et al. | |
| 6,187,040 B1 | 2/2001 | Wright | |
| 6,210,347 B1 | 4/2001 | Forsell | |
| 6,217,610 B1 | 4/2001 | Carpentier et al. | |
| 6,231,602 B1 | 5/2001 | Carpentier et al. | |
| 6,251,092 B1 | 6/2001 | Qin et al. | |
| 6,296,656 B1 | 10/2001 | Bolduc et al. | |
| 6,315,784 B1 | 11/2001 | Djurovic | |
| 6,319,281 B1 | 11/2001 | Patel | |
| 6,328,746 B1 | 12/2001 | Gambale | |
| 6,332,893 B1 | 12/2001 | Mortier et al. | |
| 6,355,030 B1 | 3/2002 | Aidrich et al. | |
| 6,361,559 B1 | 3/2002 | Houser et al. | |
| 6,368,348 B1 | 4/2002 | Gabbay | |
| 6,402,780 B2 | 6/2002 | Williamson, IV et al. | |
| 6,406,420 B1 | 6/2002 | McCarthy et al. | |
| 6,406,493 B1 | 6/2002 | Tu et al. | |
| 6,419,696 B1 | 7/2002 | Ortiz et al. | |
| 6,451,054 B1 | 9/2002 | Stevens | |
| 6,458,076 B1 | 10/2002 | Pruitt | |
| 6,461,366 B1 | 10/2002 | Seguin | |
| 6,470,892 B1 | 10/2002 | Forsell | |
| 6,503,274 B1 | 1/2003 | Howanec, Jr. et al. | |
| 6,524,338 B1 | 2/2003 | Gundry | |
| 6,530,952 B2 | 3/2003 | Vesely | |
| 6,533,772 B1 | 3/2003 | Sherts et al. | |
| 6,537,314 B2 | 3/2003 | Langberg et al. | |
| 6,547,801 B1 | 4/2003 | Dargent et al. | |
| 6,554,845 B1 | 4/2003 | Fleenor et al. | |
| 6,564,805 B2 | 5/2003 | Garrison et al. | |
| 6,565,603 B2 | 5/2003 | Cox | |
| 6,569,198 B1 | 5/2003 | Wilson et al. | |
| 6,579,297 B2 | 6/2003 | Bicek et al. | |
| 6,589,160 B2 | 7/2003 | Schweich, Jr. et al. | |
| 6,592,593 B1 | 7/2003 | Parodi et al. | |
| 6,602,288 B1 | 8/2003 | Cosgrove et al. | |
| 6,602,289 B1 | 8/2003 | Colvin et al. | |
| 6,613,078 B1 | 9/2003 | Barone | |
| 6,613,079 B1 | 9/2003 | Wolinsky et al. | |
| 6,619,291 B2 | 9/2003 | Hlavka et al. | |
| 6,626,899 B2 | 9/2003 | Houser et al. | |
| 6,626,917 B1 | 9/2003 | Craig | |
| 6,626,930 B1 | 9/2003 | Allen et al. | |
| 6,629,534 B1 | 10/2003 | St. Goar | |
| 6,629,921 B1 | 10/2003 | Schweich, Jr. et al. | |
| 6,651,671 B1 | 11/2003 | Donlon et al. | |
| 6,652,556 B1 | 11/2003 | VanTassel et al. | |
| 6,682,558 B2 | 1/2004 | Tu et al. | |
| 6,689,125 B1 | 2/2004 | Keith et al. | |
| 6,689,164 B1 | 2/2004 | Seguin | |
| 6,695,866 B1 | 2/2004 | Kuehn et al. | |
| 6,702,826 B2 | 3/2004 | Liddicoat et al. | |
| 6,702,846 B2 | 3/2004 | Mikus et al. | |
| 6,706,065 B2 | 3/2004 | Langberg et al. | |
| 6,709,385 B2 | 3/2004 | Forsell | |
| 6,709,456 B2 | 3/2004 | Langberg et al. | |
| 6,711,444 B2 | 3/2004 | Koblish | |
| 6,719,766 B1 | 4/2004 | Ryan et al. | |
| 6,723,038 B1 | 4/2004 | Schroeder et al. | |
| 6,726,716 B2 | 4/2004 | Marquez | |
| 6,726,717 B2 | 4/2004 | Alfieri et al. | |
| 6,730,121 B2 | 5/2004 | Ortiz et al. | |

(56) References Cited

U.S. PATENT DOCUMENTS

| | | |
|---|---|---|
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,338,511 B2 * | 3/2008 | Mirigian .......... A61B 17/12022 606/200 |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,431,726 B2 | 10/2008 | Spence et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Saiahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,029,556 B2 | 10/2011 | Rowe |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulia et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |

(56) References Cited

U.S. PATENT DOCUMENTS

| | | |
|---|---|---|
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Aikhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,594 B2 | 2/2015 | Maisano et al. |
| 8,961,595 B2 | 2/2015 | Alkhatib |
| 8,961,596 B2 | 2/2015 | Maisano et al. |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Saiahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0103532 A1 | 6/2002 | Langberg et al. |
| 2002/0087048 A1 | 7/2002 | Brock et al. |
| 2002/0107531 A1 | 8/2002 | Schreck et al. |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0059413 A1 | 3/2004 | Argento |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |

(56) References Cited

U.S. PATENT DOCUMENTS

| | | |
|---|---|---|
| 2004/0162610 A1 | 8/2004 | Liska et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0225233 A1 | 11/2004 | Frankowski et al. |
| 2004/0243227 A1 | 12/2004 | Starksen et al. |
| 2004/0260317 A1 | 12/2004 | Bloom et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107671 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1 | 12/2005 | Corradi et al. |
| 2005/0267571 A1 | 12/2005 | Spence |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0229708 A1 | 10/2006 | Powell et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010857 A1 | 1/2007 | Sugimoto et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0112425 A1 | 5/2007 | Schaller |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086164 A1 | 4/2008 | Rowe |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |

(56) References Cited

U.S. PATENT DOCUMENTS

| | | |
|---|---|---|
| 2008/0281353 A1 | 11/2008 | Aranyi et al. |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2009/0028670 A1 | 1/2009 | Garcia et al. |
| 2009/0043381 A1 | 2/2009 | Macoviak et al. |
| 2009/0054969 A1 | 2/2009 | Salahieh et al. |
| 2009/0062666 A1 | 3/2009 | Jackson |
| 2009/0076547 A1 | 3/2009 | Sugimoto |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0093670 A1 | 4/2009 | Annest et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0292353 A1 | 11/2009 | Yoganathan et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0063542 A1 | 3/2010 | van der Burg et al. |
| 2010/0063550 A1 | 3/2010 | Felix et al. |
| 2010/0063586 A1 | 3/2010 | Hasenkam |
| 2010/0070028 A1 | 3/2010 | Sugimoto |
| 2010/0076499 A1 | 3/2010 | McNamara et al. |
| 2010/0094248 A1 | 4/2010 | Nguyen et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168645 A1 | 7/2010 | Wright |
| 2010/0174358 A1 | 7/2010 | Rabkin et al. |
| 2010/0179574 A1 | 7/2010 | Longoria et al. |
| 2010/0210899 A1 | 8/2010 | Schankereli |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0292785 A1 | 11/2010 | Seguin et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0015476 A1 | 1/2011 | Franco |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0060407 A1 | 3/2011 | Ketai |
| 2011/0066231 A1 | 3/2011 | Cartledge et al. |
| 2011/0067770 A1 | 3/2011 | Pederson et al. |
| 2011/0071626 A1 | 3/2011 | Wright |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 6/2011 | Cartledge et al. |
| 2011/0184510 A1 | 7/2011 | Maisano et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0029627 A1 | 2/2012 | Salahieh et al. |
| 2012/0035712 A1 | 2/2012 | Maisano et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0179086 A1 | 7/2012 | Shank et al. |
| 2012/0191123 A1* | 7/2012 | Brister .............. A61F 5/0043 606/191 |
| 2012/0191182 A1 | 7/2012 | Hauser et al. |
| 2012/0203336 A1 | 8/2012 | Annest |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0310840 A1 | 12/2012 | Colombo et al. |
| 2012/0323313 A1 | 12/2012 | Seguin |
| 2013/0018459 A1 | 1/2013 | Maisano et al. |
| 2013/0030522 A1 | 1/2013 | Rowe et al. |
| 2013/0046373 A1 | 2/2013 | Cartledge et al. |
| 2013/0046380 A1 | 2/2013 | Maisano et al. |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0268069 A1 | 10/2013 | Zakai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2014/0081394 A1 | 3/2014 | Keranen et al. |
| 2014/0088368 A1 | 3/2014 | Park |
| 2014/0094626 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |

(56) References Cited

U.S. PATENT DOCUMENTS

| | | |
|---|---|---|
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0350662 A1 | 11/2014 | Vaturi |
| 2014/0379006 A1 | 12/2014 | Sutherland et al. |
| 2015/0018940 A1 | 1/2015 | Quill et al. |
| 2015/0025553 A1 | 1/2015 | Del Nido et al. |
| 2015/0051697 A1 | 2/2015 | Spence et al. |
| 2015/0081014 A1 | 3/2015 | Gross et al. |
| 2015/0112429 A1 | 4/2015 | Khairkhahan et al. |
| 2015/0112432 A1 | 4/2015 | Reich et al. |
| 2015/0119936 A1 | 4/2015 | Gilmore et al. |
| 2015/0119979 A1 | 4/2015 | Maisano et al. |
| 2015/0127097 A1 | 5/2015 | Neumann et al. |
| 2015/0164637 A1 | 6/2015 | Khairkhahan et al. |
| 2015/0182336 A1 | 7/2015 | Zipory et al. |
| 2015/0209558 A1* | 7/2015 | Charlebois ........ A61M 25/0155 604/101.02 |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2015/0352337 A1* | 12/2015 | Iga ..................... A61B 1/00082 600/116 |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0224489 A1 | 8/2017 | Starksen et al. |
| 2017/0245993 A1 | 8/2017 | Gross et al. |
| 2018/0049875 A1 | 2/2018 | Iflah et al. |
| 2018/0318080 A1 | 11/2018 | Quill et al. |
| 2019/0038411 A1 | 2/2019 | Alon |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | WO 2008/112740 | 9/2008 |
| WO | 2010000454 A1 | 1/2010 |
| WO | WO 2012/004679 | 1/2012 |
| WO | WO 2012/178115 | 12/2012 |
| WO | 2012176195 A3 | 3/2013 |
| WO | 2014064964 A1 | 5/2014 |
| WO | WO 2014/134183 | 9/2014 |

OTHER PUBLICATIONS

Agarwal et al. International Cardiology Perspective Functional Tricuspid Regurgitation, Circ Cardiovasc Interv 2009;2;2;565-573 (2009).

Ahmadi, A., G. Spillner, and Th Johannesson, "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success—midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio-thoracic Surgery 17 (2000) 201-205.

O'Reilly S et al., "Heart valve surgery pushes the envelope," Medtech Insight 8(3): 73, 99-108 (2006).

Odell JA et al., "Early Results o4yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

(56) References Cited

OTHER PUBLICATIONS

Tajik, Abdul, "Two dimensional real-time ultrasonic imaging of the heart and great vessels", Mayo Clin Proc. vol. 53:271-303, 1978.

* cited by examiner

SYSTEM AND METHOD FOR RESHAPING RIGHT HEART

CROSS REFERENCE TO RELATED APPLICATION

The present application claims priority to U.S. patent application Ser. No. 62/272,882, filed Dec. 30, 2015, which is hereby incorporated by reference in its entirety.

TECHNICAL FIELD

The present teachings generally relate to an inflatable device, and its use in reshaping the right heart, reducing tricuspid regurgitations, or/and delaying progression of heart failure due to tricuspid regurgitation.

BACKGROUND

Tricuspid valve diseases relate to conditions in which the valve between the two right heart chambers (i.e., the right ventricle and the right atrium) doesn't function properly and these diseases often occur with other heart valve problems. Examples of the tricuspid valve diseases include tricuspid valve regurgitation, tricuspid valve stenosis, tricuspid valve atresia, and the Ebstein's anomaly. In the tricuspid valve regurgitation, the tricuspid valve doesn't close properly and blood flows back into the right atrium; in the tricuspid valve stenosis, the tricuspid valve is narrowed and reduces the amount of blood flowing into the right ventricle; in the tricuspid atresia, a congenital heart disease, a solid wall of tissues blocks the blood from flowing between the two right heart chambers; and in the Ebstein's anomaly, a malformed tricuspid valve situates at a position lower than the normal position in the right ventricle and causes blood to flow back into the right atrium. There are other tricuspid valve diseases generally known to a person with ordinary skill in the art and these tricuspid valve diseases are also included in the present teachings.

A tricuspid valve disease can be corrected by an annuloplasty ring. In some instances, this device is preferred for surgically repairing a defective tricuspid valve. An annuloplasty ring is an anatomically-correct three-dimensional (3D) ring and can flexibly conform to the heart valve opening. This ring is implanted into a defective tricuspid valve and reduces the valve opening. Properly implanted, an annuloplasty ring allows the valve to open and close properly.

Tricuspid valve repair surgeries can be done in one of the following two ways: a minimally invasive surgery or an open-heart surgery. A minimally invasive method involves making a small incision in the upper or lower chest and inserting a valve repairing system/device percutaneously. After the valve is repaired, the incision is closed with dissolving sutures. Comparing to an open-heart surgery, advantages of a minimally invasive approach include a shorter recovery time, less post-operation pain, and earlier return to work and normal daily activities.

However, there are drawbacks in valve replacement therapies and, as a result, needs exist for repairing a diseased tricuspid valve percutaneously.

SUMMARY

One aspect of the present teachings provides a device configured to be positioned against a right heart. The device has a collapsed delivery profile and an inflated deployment profile. The flexible outer layer is configured to prevent moisture and gas from crossing the flexible outer layer. The device comprises a flexible outer layer encasing a cavity. The cavity is configured to be filled with an injection medium. The device further includes an injection port configured to be used to allow the injection medium enter into the cavity.

In one embodiment, the device has a portion of the flexible outer layer which inflates to a greater extent than the rest of the flexible outer layer.

In another embodiment, the flexible outer layer further comprises a first component and a second component, wherein the first component and the second component are binding together to form a waist. The first component is configured to be positioned against the right atrium. The second component is configured to be positioned against a right ventricle. The waist is configured to be positioned outside of the tricuspid annulus. In its deployed configuration, the waist of the flexible outer layer inflates to a less extent than the first and second components.

Another aspect of the present teachings provides a device configured to be positioned against a right heart, wherein the device has a collapsed delivery profile and an inflated deployment profile. The device comprises a flexible outer layer encasing a primary cavity and a secondary cavity radially outside of the primary cavity. The primary cavity is configured to be filled with an injection medium. The secondary cavity is configured to be filled with tissue binding adhesives. A barrier separates the primary and second cavities, preventing moisture and gas from crossing the barrier. And a portion of the flexible outer layer outside of the secondary cavity has a plurality of pores, allowing the tissue binding adhesive to exit the secondary cavity to the outside of the flexible outer layer.

In one embodiment, when filled with injection medium, the barrier separating the primary and second cavities expands to a greater extent than the portion of the flexible outer layer outside of the secondary cavity.

DETAILED DESCRIPTION

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the Applicant(s) to restrict or in any way limit the scope of the appended claims to such details. While various processes are described with reference to steps and sequences in the following disclosure, the steps and sequences of steps should not be taken as required to practice all embodiments of the present teachings.

As used herein, the term "lumen" means a canal, a duct, or a generally tubular space or cavity in the body of a subject, including a vein, an artery, a blood vessel, a capillary, an intestine, and the like. The term "lumen" can also refer to a tubular space in a catheter, a sheath, a hollow needle, a tube, or the like.

As used herein, the term "proximal" shall mean close to the operator (less into the body) and "distal" shall mean away from the operator (further into the body). In positioning a medical device inside a patient, "distal" refers to the direction away from a catheter insertion location and "proximal" refers to the direction close to the insertion location.

As used herein, the term "wire" can be a strand, a cord, a fiber, a yarn, a filament, a cable, a thread, or the like, and these terms may be used interchangeably.

As used herein, the term "sheath" may also be described as a "catheter" and, thus, these terms can be used interchangeably.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and attached claims are approximations. At the very least and not as an attempt to limit the application of the doctrine of equivalents to the scope of the attached claims, numerical parameters should be read in light of the number of reported significant digits and the application of ordinary rounding techniques.

The present teachings relate to devices and methods for treating a tricuspid valve regurgitation percutaneously. A person with ordinary skill in the art would recognize that the figures and description thereto refer to various embodiments of the present teachings and, unless indicated otherwise by their contexts, do not limit the scope of the attached claims.

Figure 1:
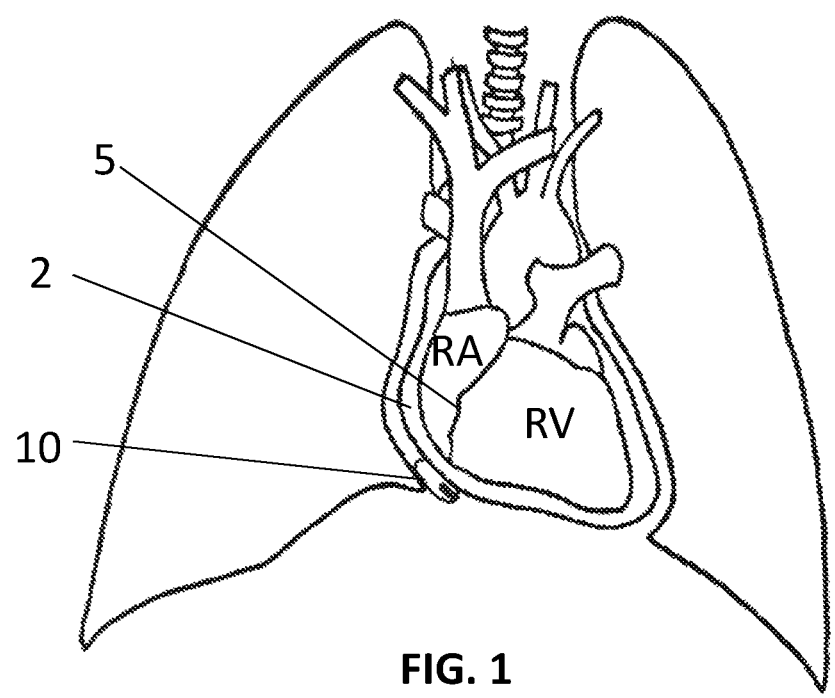
FIG. 1 is a perspective view of an embodiment of the present teachings where an inflatable balloon is positioned against the right heart free wall according to the present teachings.

An aspect of the present teachings relates to methods of reducing the size of the right heart, and subsequently reducing the tricuspid regurgitation. In various embodiments, the method includes deploying a balloon (10) through a percutaneous subxiphoid approach to the outside of the pericardium (2) as illustrated in FIG. 1. The balloon (10) squeezes the right side of the heart, both the right atrium (RA) and the right ventricle (RV). As a consequence, the tricuspid annulus changes it shape, which leads to more coaptation among the leaflets of the tricuspid valve (5).

In various embodiments, the balloon is positioned inside or outside of the pericardium. In various embodiments, the balloon is positioned approximately to the anterior and posterior commissure with a small portion, such as 30%, against the right atrium and a relatively larger portion against the right ventricle. In various embodiments, the balloon is anchored to the sternum. In various embodiments, the balloon is shaped to be self-anchoring, self-aligning, or self-stabilizing. In some embodiments, the balloon in its deployed configuration includes an indentation. In certain embodiments, the indentation is in a shape of wedge. In certain embodiments, the indentation is configured to fit the heart into the wedge when the balloon is in its deployed configuration. In particular embodiments, the wedge pushes posteriorly on the anterior portion of the right heart. In particular embodiments, the balloon is stabilized between the heart and the sternum by the wedge cupping with the right heart.

Figure 2:
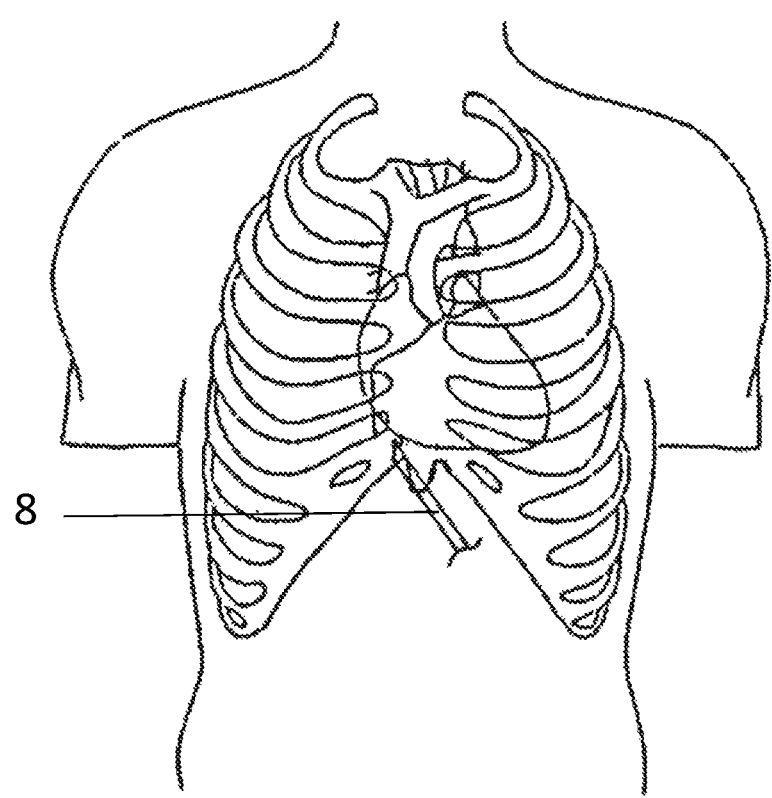
FIG. 2 is a perspective view of an embodiment of the present teachings where a needle is used to puncture subxiphoid to access the treatment space according to the present teachings.

FIG. 2 illustrates insertion of a needle (8) to the space between the heart and the sternum. According to some embodiments of the present teachings, the access to the space is done through a subxiphoid approach. The procedure starts with a small vertical incision to the left of the subxiphoid. A puncture through the skin and subcutaneous tissue is made straight or at a 45-degree angle pointing toward the right shoulder. One skilled in the art should understand that the puncture is done by using a Tuohy needle, with appropriate endocardial and/or fluoroscopy guidance. Additionally contrasts should be used to ascertain the puncture location.

In various embodiments, access for an insertion catheter is created through a needle and wire exchange. In some embodiments, a needle is used to puncture the chest cavity starting from below the xiphoid process and angling the needle superior and left. In some embodiments, a needle is used to puncture the chest cavity through the 5th or 6th intercostal space on the left side of the sternum. In some embodiments, once a needle is passed through the sternum, a wire is advanced through the needle into the space between the sternum and the pericardial sac. In various embodiments, the wire is specially designed to help remove any adhesions between the pericardium and the sternum. In some embodiments, the wire is left behind and the needle is removed. In various embodiments, an insertion catheter is advanced over the wire and into the target region of the anatomy. In some embodiments, the insertion catheter includes a dilating sheath or dilating tip designed to increase the diameter of the needle hole. In some embodiments, a separate dilating member is used prior to insertion of the catheter. In some embodiments, a fluid is injected into the target space of the anatomy in order to facilitate the subsequent inflation of the bladder. In some embodiments, the fluid is saline or nitrogen gas. In some embodiments, the fluid includes a biocompatible, bio-resorbable lubricant.

In various embodiments, access for an insertion catheter is accomplished through a novel modification of a pericardiocentesis kit. In some embodiments, a needle is advanced through the sternum and through the pericardium as is commonly done to aspirate effusions from the pericardium. In some embodiments, a wire is advanced through the needle and into the pericardial space and the needle is retracted out of the body. In some embodiments, an access catheter is advanced over the wire. In various embodiments, the access catheter is designed with a blunted tip such that it passes through the sternum but does not dilate the hole in the pericardium created by the needle. In some embodiments, the access catheter is advanced through the sternum and up to but not through the pericardium. In some embodiments, the wire is withdrawn and the catheter is repositioned in order to deliver the balloon.

In various embodiments, the delivery of the access catheter is aided by fluoroscopy, transesophageal echocardiography, or transthoracic echocardiography. In some embodiments, the delivery catheter or delivery system includes piezo electric elements designed to function as a specially designed echo probe. In some embodiments, the access catheter delivery system is designed to engage a separate and commercially available TTE probe for imaging assistance during the procedure.

In various embodiments, the access to the space between the pericardium and the heart chambers is facilitated by an indwelling catheter in the right heart. In some embodiments, the right heart catheter is designed to create a small puncture in the right atrial appendage. In some embodiments, the right heart catheter is used to inject a predetermined amount of saline or other fluid into the pericardial space. In some embodiments, the fluid is echogenic. In some embodiments, the fluid is used to create separation between the right heart and the pericardium. In some embodiments, the fluid is injected into the pericardium and then aspirated back through the access catheter or through the right heart catheter. In some embodiments, a space is created between the pericardium and the right heart by a right heart catheter. In certain embodiments, the right heart catheter is designed to grasp a portion of the right heart, for example, the right atrial appendage, or the anterior wall of the right atrium. In some embodiments, the right heart catheter is designed to grasp the anterior wall of the right heart above the plane of the right coronary artery. In certain embodiments, the right heart catheter is retracted by 2-3 cm in order to create some space between the pericardium and the right heart.

In various embodiments, the distal end of the insertion needle (8) is positioned outside of the pericardium. In other embodiments, the distal end of the insertion needle (8) is further advanced slightly to puncture the pericardium and reach inside the pericardial space.

Figure 3:
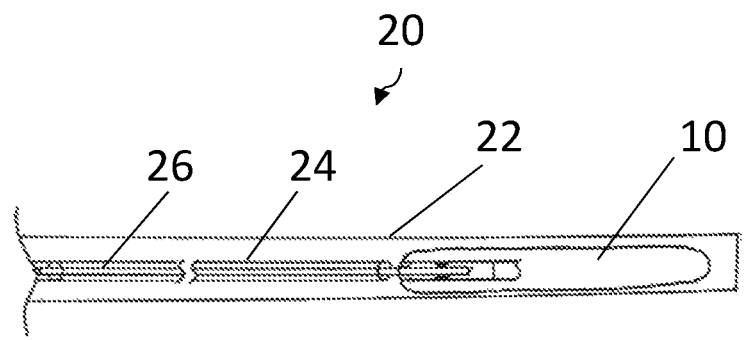
FIG. 3 is an embodiment of the inflatable balloon in its delivery profile and attached to a delivery system in accordance with the present teachings.
Figure 4:
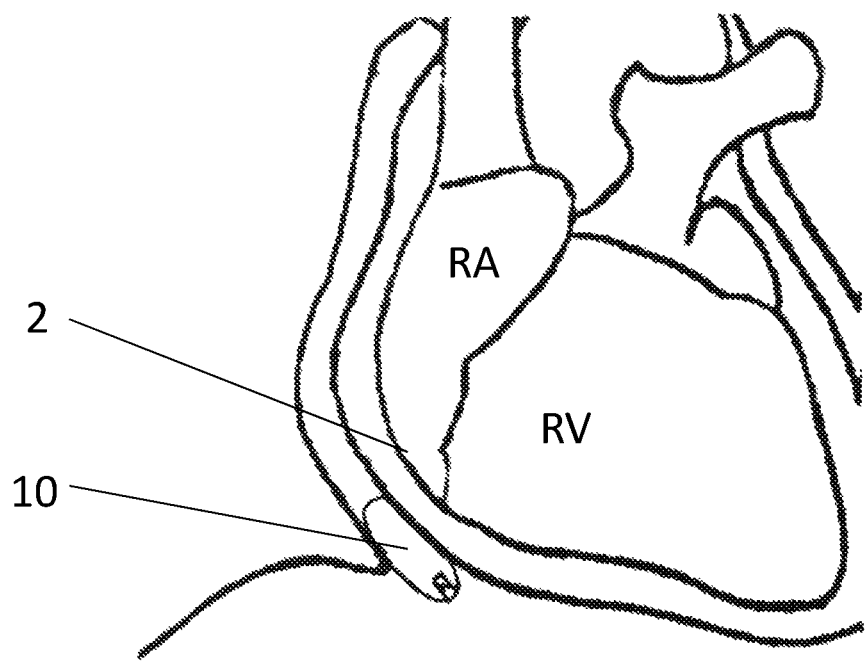
FIG. 4 is an embodiment of the inflatable balloon positioned against the right heart free wall according to the present teachings.

Another aspect of the present teachings provides an inflatable balloon (10) that can be deployed at a treatment location, as shown in FIG. 4. In various embodiments, the inflatable balloon (10) has a cavity (37) (FIG. 5) encased by at least one layer of a flexible material. In some embodiments, the inflatable balloon (10) has a delivery state where it is housed and delivered through a delivery system (20) as shown in FIG. 3. In one embodiment, the delivery system (20) includes an access sheath (22), a delivery catheter (24), and an injection catheter (26). In some embodiments, the inflatable balloon (10) has a deployed state, where it is filled with an injectable medium, such as a liquid, a gel, a gas, foam, or another medium. In some embodiments, the delivery state of the inflate balloon (10) is referred to as a state where the device is completely free of injectable medium. Alternatively, in some embodiments, the balloon (10) is partially filled with some injectable medium. In some embodiments, any state that is greater in size than the delivery state is considered to be a deployed state.

In various embodiments, as shown in FIG. 4, at its deployed state, the balloon (10) is positioned against the right heart anterior free wall approximate to the outside of the tricuspid valve (5) annulus location (See, FIG. 1). As shown in FIG. 4, a portion of the balloon (10) is placed and compresses against the right atrium, and another portion of the balloon (10) is placed and compresses against the right ventricle. In some embodiments, the balloon (10) at its deployed state is configured to compress the right side of the heart, changes the profile of the tricuspid annulus, and, as a result, improves the coaptation of the tricuspid leaflets and reduces tricuspid regurgitation. One skilled in the art should understand that the deployed state of the balloon (10) could vary from a patient to another patient due to the individual anatomy and the amount of compression needed to achieve a reduction in tricuspid regurgitation. Thus, the amount of the medium injected inside the cavity (37) of the inflatable balloon (10) is determined based on each patient's needs and controlled by a clinician.

According to some embodiments, the medium filled inside the cavity (37) of the balloon (10) could be an injectable medium, such as a liquid, a hydrogel, a gas, or foam. In an embodiment, other materials or structures, that is capable of maintaining its volume as well as changing its shape to conform to the anatomic space at the implanting location while under compression, could also be used. In another embodiment, the injectable medium is capable of reducing its volume while under compression, and increasing its volume after the compression is removed, for example, a material capable of undergoing a phase change from a first volume to a second volume at the temperature and/or pressure ranges inside a body cavity (37) may also be used.

Figure 5:
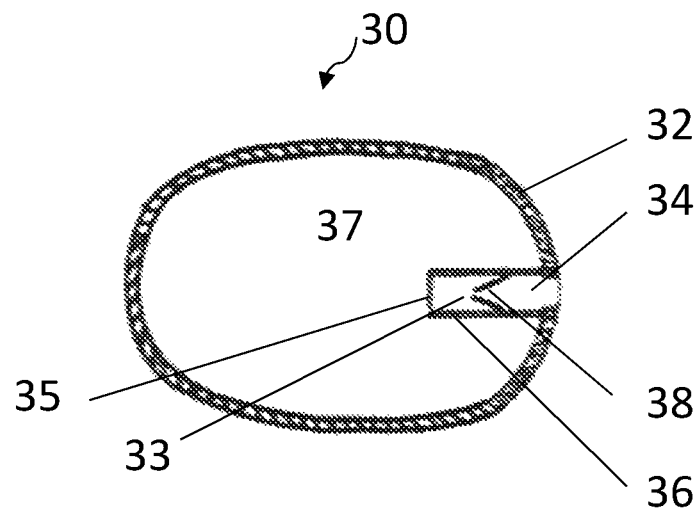
FIG. 5 is an embodiment of the inflatable balloon in its delivery profile according to the present teachings.

Now referring to FIG. 5, where an exemplary embodiment of an inflatable balloon (30) is illustrated in its deployed profile. In various embodiments, the inflatable balloon (30) comprises a flexible wall (32) and an injection port (34). In various embodiments, the flexible wall (32) is configured to transfer the pressure from the inside to the outside of the balloon (10). As a result, in some embodiments, the inflatable balloon (10) exerts a force to the heart. In various embodiments, the flexible wall (32) is flexible. In some embodiments, the flexible wall (32) allows shape change of the balloon (30) while the balloon (30) is exposed to an external pressure from the anatomy. In various embodiments, the flexible wall (32) is stiff enough to hold the pressure exerted by the medium inside the balloon (30).

Continue referring to FIG. 5, according to some embodiments, the injection port (34) joins, releasably, a medium injection catheter (26) (See, FIG. 3). As later described, in some embodiments, once joined, the injection catheter (26) is configured to push, pull, or otherwise manipulate the inflatable balloon (30). In some embodiments, the injection catheter (26) is configured to deliver a medium into the cavity (37) of the balloon (30).

According to some embodiments, the flexible wall (32) of the device comprises at least one gas barrier layer. According to some embodiments, the flexible wall (32) comprises at least one moisture barrier layer. According to some embodiments, the gas barrier layer and moisture barrier layer are laminated together. In some embodiments, the gas barrier is constructed as an external layer of the flexible wall (32). In some embodiments, the moisture barrier is constructed as an internal layer of the flexible wall (32). In other embodiments, the moisture barrier is constructed as an external layer of the flexible wall (32). In other embodiments, the gas barrier is constructed as an internal layer of the flexible wall (32). In other embodiments, the gas barrier material and moisture barrier material are blended together to form a single barrier layer. Yet in other embodiments, more than one layer of the gas barrier and/or more than one layer of the moisture barrier layer are incorporated. In some embodiments, the more than one layer of the gas barrier and the more than one layer of the moisture barrier layer are arranged in an alternating manner. In yet other embodiments, any other arrangements are equally applicable as long as they are suitable for the purpose of the present teachings and their manufacturing capability.

A variety of gas barrier materials, including polyvinylidene chloride, ethyl vinyl alcohol, fluoropolymers, or etc., can be used for constructing a device of the present teachings. Gas barrier materials are generally relatively stiff, have high moisture vapor permeability, and low impact strength. Consequently, a layer of flexible material with high moisture barrier and high impact strength should also be incorporated into the flexible wall (32) of the device.

A variety of moisture barrier materials, including polyamide, polyethylene, polypropylene, polyurethane, polyamide/polyester copolymer, polystyrene/polybutadiene copolymer, and etc., can be used for constructing a device of the present teachings. The moisture barrier materials are generally flexible and have high impact strength.

In some embodiments, an additional reinforcement layer is incorporated into the flexible wall (32) in order to enhance the structural integrity of the device. In some embodiments, the reinforcement layer has high impact strength. In certain embodiments, the reinforcement layer is made of a polymer, including polyurethane, EVA, PE, polypropylene, or silicone. In various embodiments, the reinforcement layer is an external layer of the flexible wall (32). In various embodiments, the reinforcement layer is an internal layer of the flexible wall (32). In various embodiments, the reinforcement layer is a middle layer of the flexible wall (32). In some embodiments, the flexible wall (32) includes more than one reinforcement layer. In certain embodiments, at least one of the more than one reinforcement layers is between a gas barrier layer and a moisture barrier layer.

In some embodiments, the device have three, four, five, or more layers including a gas barrier layer, a moisture barrier layer, and one or more reinforcement layers. In some embodiments, the device has multiple gas barrier layers and/or multiple moisture barrier layers, arranged in a sequential or non-sequential arrangement.

In various embodiments, the overall thickness of the flexible wall (32) is preferably minimized. In some embodiments, the overall thickness of the flexible wall (32) ranges between 0.003 to 0.03 inches. In some embodiments, each layer of the flexible wall (32) has a same thickness. In some embodiments, at least two layers have different thickness. In certain embodiments, each layer of the flexible wall (32) has a different thickness from the other layers.

The layers of the flexible wall (32) can be made in any number of ways known to those skilled in the art, including, but not limited to, lamination, co-extrusion, dip molding, spray molding, or the like. In various embodiments, the flexible wall (32) is made by laminating two or more layers together. Lamination can be achieved through many techniques known to those skilled in art. In some embodiments, the lamination is achieved by using heating, solvents, adhesives, tie layers, or other like methods.

One skill in the art would understand that the material used to construct the flexible wall (32) of the device is sufficiently flexible in the thickness ranges selected for the present teachings. Since the device is subject to external pressures, the device's material in various embodiments is able to transmit the pressure from the sternum to the right heart. In various embodiments, the material used to construct the flexible wall (32) is selected to produce an appropriate compression to the right heart. In various embodiments, the pressure and volume of the inflation medium (injection medium) is selected to produce an appropriate compression to the right heart. For example, in its deployed profile, the device is sufficiently stiff to compress the right heart. In some embodiments, the compression leads to a change of the profile of the tricuspid annulus. In some embodiments, the device is flexible enough to accommodate the right heart expansion during the diastolic cycles.

According to some embodiments, the right heart pressure, such as the right ventricle pressure, is closely monitored during the balloon expansion in order to prevent from over-pressuring the right heart. For example, during the balloon expansion, the pulmonary capillary wedge pressure (PCWP) can be monitored and the PCWP can sometimes serve as a good indicator for the right ventricle pressure. When it shows that the right ventricle is over pressured, for example, beyond 40 mmHg, a clinician can deflate the balloon.

According to some other embodiments of the present teachings, the balloon is designed in such way that after deployed, it can still be reattached to a catheter in order to further inflate or deflate the balloon to achieve the optimum treatment result. For example, a balloon can include an injection port which can be reattached by an injection catheter after the procedure. In another example, a balloon can also include a lead which can be left behind and used to be re-attached for pressure adjustment after the procedure.

According to other embodiments of the present teachings, a pumping mechanism between the components of the balloons is also incorporated in the design in order to allow fluid transfer between the components. In some embodiments, such pumping mechanism allows pressure adjustment in each component of the balloon and can be used to avoid over pressuring certain part of the heart, or create a messaging effect to the heart.

Figure 6:
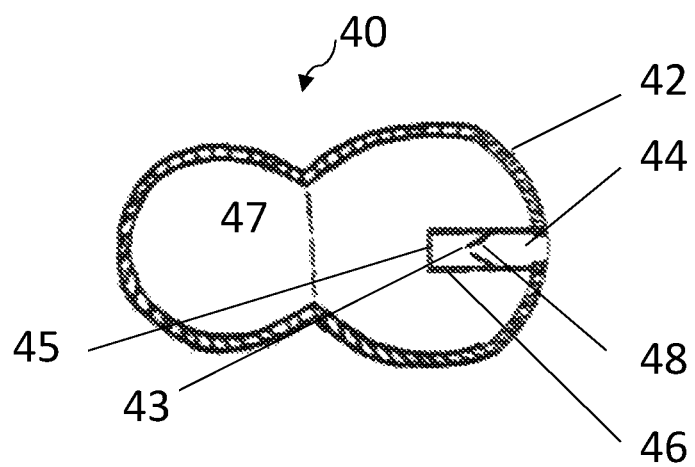
FIG. 6 is an embodiment of the inflatable balloon in its delivery profile according to the present teachings.

In some embodiments, the flexible wall (32) comprises a continuous layer of material. In some embodiments, such as FIG. 6, the flexible wall (42) comprises a first component and a second component, where the first and second components are bonded together. Once injected with the medium, the first component and second component of the balloon (40) expands, while the bonding seam between the first component and second component, remains unchanged, or only slightly stretched, forming a waist in its deployed profiled, such as shown in FIG. 6. In some embodiments, the bonding seam is configured to be positioned outside of the tricuspid valve (5) annulus.

One skilled in the art should understand that the two components can be identical or different in sizes. In some embodiments, the components to be deployed against the right ventricle are larger than the component to be deployed against right atrium. According to some embodiments, the seams are accomplished in any of a variety of manners known to those skilled in the art. In certain embodiments, the bonding of the two components are achieved by using heat bonding, chemical bonding, mechanism bonding, and the like. One skilled the art should understand that more than two components can be included in forming the device. Thus, the embodiments disclosed herein should not be viewed as limiting.

According to some embodiments, once injected with a medium of the present teachings, the balloon (10) device as illustrated in FIGS. 5-6 expand evenly in all directions. In other embodiments, the expansion of the balloon (10) is controlled with the most expansion inwardly toward the heart, and less or no expansion in other directions so that once deployed, the portion of the balloon (10) facing the heart wall expands and compresses the right heart.

According to some embodiments of the present teachings, the balloon is expanded in a sequential motion with one component expanding after another. In other embodiments of the present teachings, the balloon expansion is controlled by a dynamic pulse control, such that one component is expanded with a long pulse, and another component is expanded with a high pulse. One skilled in the art should understand that balloon expansion can be achieved by many other ways, and the exemplary approaches described herein should not be viewed as limiting to the scope of the present teachings.

In some embodiments, once inflated, the balloon (10) has an overall width of 2 mm-4 cm and an overall height of 4 mm-6 cm. In some embodiments, the portion of the balloon (10) against the right ventricle is greater than the portion of the balloon (10) against the right atrium.

In various embodiments, the balloon is designed to be compliant only up to a predetermined size and shape. After the balloon is inflated to this shape by the injectable fluid, the balloon resists further inflation. In some embodiments, the resistance to additional inflation is accomplished by the composite construction of the balloon. In some embodiments, the wall of the balloon includes fibrous members such as suture material, braided polyester fibers, nylon strands, or other materials. In some embodiments, the bladder is loosely defined as a non-compliant balloon. In some embodiments, the bladder is designed to inflate in a stepwise manner. In various embodiments, in the first step, the bladder is designed to expand in a manner that is largely flat, expanding along the contact surface of the right heart and the sternum. In some embodiments, as the inflation pressure increases and the largely flat expansion of the balloon nears its final size, the balloon expands largely by increasing in thickness. In some embodiments, the balloon includes two fluid sealed cavities/chambers. In some embodiments, the first cavity/chamber includes a large flat shape which contours to the wall of the sternum and to the shape of the heart. In some embodiments, the second cavity/chamber is designed to expand largely in the thickness dimension, thereby pushing against the sternum and the heart but not expanding in other directions.

According to various embodiments (e.g., FIG. 5), the injection port (34) of the device includes an injection tube (36) and a valve (38). The injection tube (36) creates a fluid communication path between the interior cavity (37) and the injection catheter (26). The valve (38) is configured to permit one way flow through the injection tube (36). Upon removal of the injection catheter (26), the valve (38) closes automatically and prevents the escape of the injection medium from the interior cavity (37) through the injection tube (36).

According to some embodiments, the injection tube (36) has a connected end joining to the flexible wall (32) and a free end (35) extending into the cavity (37) of the balloon (10). In certain embodiments, the tube includes a tubular lumen (33) extending from the connected end to its free end (35). The tubular lumen (33) forms a flow path for the injection medium to be delivered inside the cavity (37) of the balloon (10). In other embodiments, the valve (38) is positioned inside the tubular lumen (33) of the Tube. Although FIG. 5 illustrates a valve (38) in the middle portion of the tubular lumen (33), one skilled in the art would understand that the valve (38) can be at or near the connected end of the injection tube (36), at or near the free end (35) of the injection tube (36), or anywhere inside the lumen between the connected and free end (35) of the injection tube (36).

According to various embodiments, the injection tube (36) is made of polyethylene, Pebax, polyurethane, etc. In various embodiments, the injection tube (36) is made by a known technique in the field. In some embodiments, the injection tube (36) is made by extrusion. According to various embodiments, the valve (38) and flap are made from a flexible material such as polyurethane, silicone, or polyethylene. According to some embodiments, the bonding between the valve (38) and tube, the tube and the flexible wall (32) of the balloon (30), and the flap and the tube is achieved by a known technique in the field. In certain embodiments, the bonding is achieved through a mechanical means. In particular embodiments, the bonding is through a screw, a bolt, a clamp, or the like. In certain embodiments, the bonding is achieved through a chemical means. In particular embodiments, the bonding is achieved through an adhesive or the like. In some embodiments, the bonding is achieved through a thermal means. In particular embodiments, the bonding is achieved by ultrasonic welding, laser welding, overmolding, or the like. Other attachment methods known to the skilled artisan can also be used.

According to various embodiments of the present teachings, upon the device being filled with the medium content, the device resumes a predesigned deployed profile. In some embodiments, upon inflation, the device assumes a general spherical profile, a pillow profile, or a snow man profile with a waist. One skilled in the art should understand that an inflated device can assume any profile that is suitable for its intended function.

According to various embodiments, the valve (38) inside the injection tube (36) has a duckbill configuration. In some embodiments, the valve (38) includes a first and a second duck bill valve (38) leaflets which are attached to the tubular wall. In some embodiments, the leaflets extend in the direction toward the free end (35) of the injection tube (36) and form a pair of coaptive edges. This configuration allows a distal-direction flow to separate the coaptive edges, thereby enabling inflation of the device. Upon removal of the injection medium source, the inflation medium within the device in combination with the natural bias of the leaflets cause the leaflets to coapt, thereby preventing any proximal flow of medium through the flow path. One skilled in the art should understand that other suitable valve (38) design, such as tricuspid, flap, biased valve (38), known in the field could also be used here. Thus, the embodiments disclosed herein should not be viewed as limiting to the overall scope of the present teachings.

Figure 7:
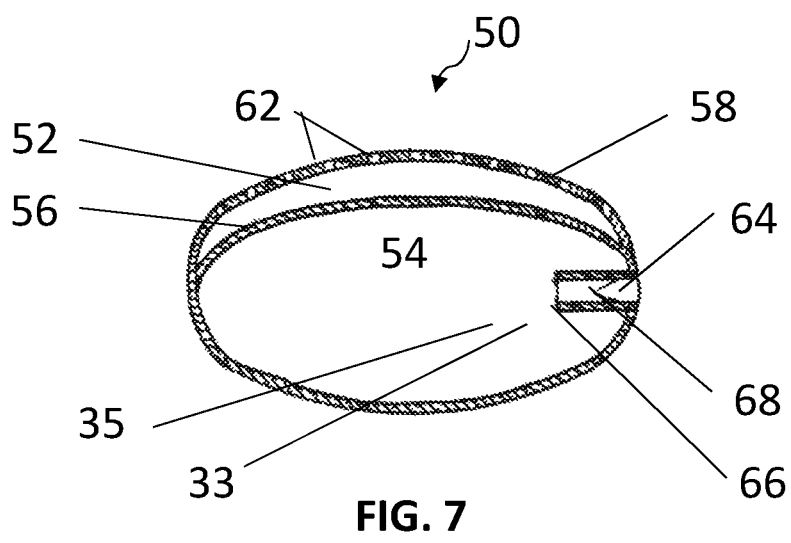
FIG. 7 is an embodiment of the inflatable balloon in its delivery profile according to the present teachings.

FIG. 7 illustrates another embodiment of the present teachings, where the balloon (50) further includes a binding mechanism that is configured to secure a deployed balloon (50) at a treatment location. As shown in the figure, the inflatable balloon (50) has two cavities. The primary cavity (54) is configured to be filled with an inject medium which causes the balloon (50) to expand. The secondary cavity (52) is configured to contain a bio-adhesive. And the secondary cavity (52) is located radially outside of the primary cavity (54) as shown. According to one embodiment, the secondary cavity (52) is located radially outside of the primary cavity (54). A barrier (56) exists between the primary and secondary cavities (52), which prevents the injection medium from exiting the primary cavity (54) and entering the secondary cavity (52). According to some embodiments, the secondary cavity (52) is covered with an external stretchable and porous layer (58). Similar to the previous embodiments, the balloon (50) includes an injection port (64), an injection tube (36) and a valve (68) disposed within the injection tube (36).

When the balloon (50) is in its delivery collapsed profile, the adhesive is stored inside the secondary cavity (52). The delivery system carries the collapsed balloon (50) into the treatment location. Once the balloon (50) is filled with injection medium, as the balloon (50) expands, the external porous layer (58) outside of the secondary cavity (52) also stretches, allowing the pores to be opened up. As the balloon (50) further expands, it squeezes the adhesive, letting it exit the pores (62). The adhesive is configured to bond the balloon (50) with the sternum.

In some embodiments, when filled with the injection medium, the barrier (56) separating the primary and second cavities (54, 52) expands more than the portion of the flexible outer wall outside of the secondary cavity (52). As a result, the difference in stretchability would allow the primary cavity (54) to expand at a greater rate than the secondary cavity, thereby pushing the tissue binding adhesive out of the pores (62) in the flexible wall (58).

In some embodiments, the balloon (50) is designed such that under certain inflation pressures, the adhesive remains inside the secondary cavity (52). Once a clinician is satisfied with the deployment and/or apposition, the balloon (50) is inflated to a final pressure and the adhesive is then pushed out to the external surface (58). In some embodiments, the adhesive is activated upon being exposed to the moisture of the anatomy.

According to one embodiment of the present teachings, the secondary cavity is configured to be positioned approximately to the right ventricle, so that after an adhesive is applied to the exterior surface, the balloon is bonded to the right ventricle. In another embodiment, the secondary cavity is configured to be positioned approximately to the right atrium, so that the adhesive is used to bond the balloon to the right atrium of the heart.

Figure 8:
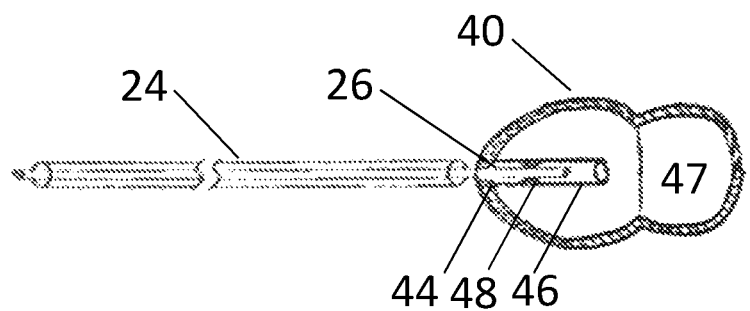
FIG. 8 is an embodiment of the inflatable balloon attached to a delivery system in accordance with the present teachings.

FIG. 8 further illustrates a balloon delivery system configured to join the balloon (40) at its injection port (44). In various embodiments, the balloon delivery system controls the movement of the balloon (40) and injects the inflation medium into the cavity (47) of the inflatable balloon (40). According to some embodiments, the balloon delivery system comprises an elongate delivery catheter (24) having a proximal end and a distal end. The delivery catheter (24) is configured to slide through an access sheath (22) (not shown) placed at the treatment location. Thus, the delivery catheter (24) preferably has an outside diameter of no more than about 8 mm. The length of the delivery catheter (24) may vary, depending upon each patient. In general, an axial length of delivery catheter (24) is within the range of from about 1" to about 10" for adult patients.

According to various embodiments, the delivery catheter (24) has a central lumen extending axially therethrough. The central lumen axially slideably receives an injection catheter (26) for filling the balloon (40). The injection catheter (26) comprises a tubular body having a proximal end, a distal end, and a medium injection lumen extending throughout the length from its distal end to a proximal hub where a connector is typically used for coupling the proximal hub to a source of inflation medium.

According to various embodiments, the injection catheter (26) extends distally, or retracts proximally, independent of the delivery catheter (24). The distal end of the injection catheter (26) has a generally tubular shape and is configured to be positioned within the valve (48) inside the injection port (44) of the balloon (40). The distal end of the delivery catheter (24) is dimensioned such that it fits through the injection port (44) of the balloon (40). In some embodiments, the delivery catheter (24) further includes a distal stop surface configured to stop the proximal movement of the device as shown in FIG. 8.

FIG. 8 illustrates an embodiment of the present teachings where the balloon delivery system is fully engaged with the balloon (40). As illustrated, the distal end portion of the injection catheter (26) is fit inside the injection tube (46) and positioned across the valve (48). In some embodiments, the distal end portion of the injection catheter (26) is capable of opening the valve (48). The distal end of the injection catheter (26) is within the injection tube (46) and distal to the valve (48). The distal end of the delivery catheter (24) contacts the proximal end of the injection tube (46). In some embodiments, the balloon (40) is pushed distally, retracted proximally, torqued radially, and otherwise manipulated by the balloon delivery system.

In various embodiments, the valve (48) inside the injection tube (46) of the balloon (40) has a mechanism that prevents the injection medium from back-flowing to the outside of the balloon (10). According to some embodiments, once the injection catheter (26) is placed inside the injection port (44), a clinician can inject the inflation medium into the cavity (47) of the balloon (40).

Figure 9:
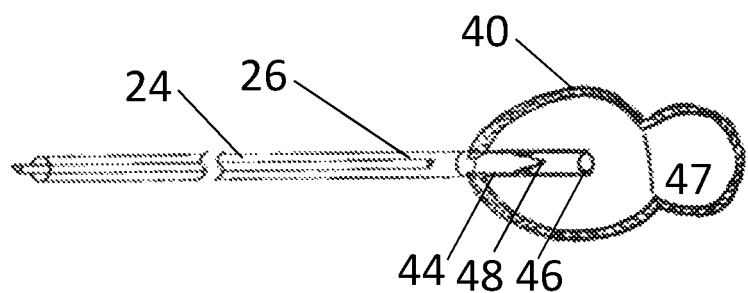
FIG. 9 is an embodiment of the inflatable balloon disengaging from a delivery system in accordance with the present teachings.

After the balloon (40) is inflated to a desired size, a clinician in various embodiments stops the medium injection and removes the injection catheter (26). As shown in FIG. 9, with the delivery catheter (24) remains steady, the injection catheter (26) can be withdrawn proximally and exit the injection port (44) of the balloon (40). The one-way valve (48) inside the injection port (44) closes automatically and seals the injection medium inside the balloon (40).

Figure 10:
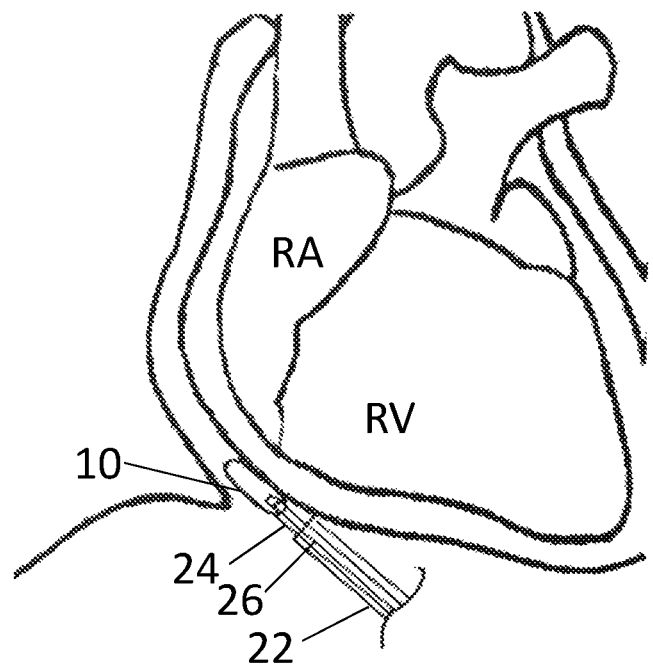
FIG. 10 is a perspective view of an embodiment of the present teachings where an inflatable balloon is delivered to the treatment location via a delivery system.
Figure 11:
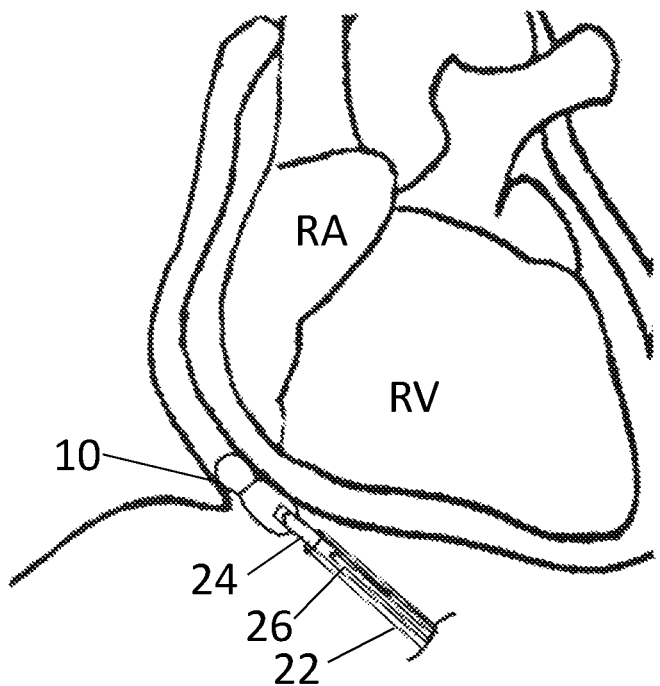
FIG. 11 is a perspective view of an embodiment of the present teachings where an inflatable balloon is deployed at the treatment location via a delivery system.

FIGS. 10-11 illustrate a deployment process of the balloon (10). As shown in FIG. 10, an access sheath (22) is first placed at the treatment location following a subxiphoid puncture described above. According to some embodiments, the access sheath (22) is used to slideably carry the balloon delivery system assembly. In some embodiments, the balloon delivery system assembly slides from a proximal end of the access sheath (22) to its distal portion after proper placement of the access sheath (22). In some embodiments, during delivery, the deflated balloon (10) is rolled around a distal end portion of the injection catheter (26) and carried within the tubular lumen of the access sheath (22) during the placement.

As shown in FIG. 10, once the system is properly positioned, the access sheath (22) is retracted proximally with respect to the balloon delivery system (20) in order to expose the deflated balloon (10). A medium is then introduced distally from the proximal hub of the injection catheter (26) to inflate the balloon (10) to an intended degree.

Following the inflation of the balloon (10), as shown in FIG. 11, the injection catheter (26) is disengaged from the injection port (34) of the balloon (10) by retracting the injection catheter (26) with respect to the delivery catheter (24). A distal stop surface on the delivery catheter (24) prevents the proximal movement of the balloon (10) as the injection catheter (26) is proximally retracted. The balloon delivery system (20) is thereafter removed from the patient, leaving the inflated balloon (10) within the body.

Figure 12:
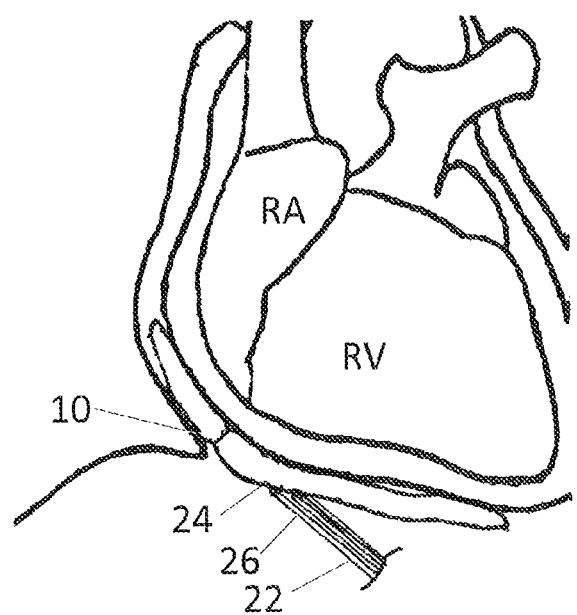
FIG. 12 is a perspective view of an embodiment of the present teachings where an inflatable balloon is deployed at the treatment location via a delivery system.

In various embodiments, the balloon device expands in a step-wise fashion. In some embodiments, the balloon device expands to a first length. In some embodiments, the balloon device expands to a first width. In some embodiments, the balloon expands to a first length first and a first width second. In some embodiments, the balloon expands to a first width first and a first length second. In certain embodiments, the first length is predetermined. In certain embodiments, the first length is adjustable according to the patient's need. For example, as shown in FIG. 12, the first length can be approximately the length of the pericardial cavity. In another example, as shown in FIG. 12, the width can be the width of the pericardial cavity. In some embodiments, the first width varies along the length of the balloon. As such, in certain embodiments, the balloon expands inwardly toward the right atrium. In certain embodiments, the balloon expands inwardly toward the right ventricle. Although FIG. 12 shows a particular length and width of a balloon device, one with ordinary skill in the art would understand that the length or/and the width of the balloon device can be greater or less than what are shown in FIG. 12.

One skilled in the art should understand that the devices disclosed above are merely embodiments of the present teachings. For example, the balloons illustrated in the drawings show only one injection port for inflation. One skilled in the art should understand that more than one injection ports can be incorporated in the balloon design without departing from the scope of the present teachings. In another example, the implantation of the balloon at a desired treatment site is done through a subxiphoid puncture procedure. An alternative to such implantation route can be to insert the balloon into the right atrium through a standard right heart catheterization procedure followed by a puncture to the heart wall from inside the right atrium. A further alternative can be to insert the balloon into the right atrium, then to extend through the tricuspid valve into the right ventricle, and finally to puncture through the right ventricular wall. Other alternative implantation route(s) can also be incorporated, and all of which should be considered as part of the present teachings.

The methods and devices disclosed above are useful for treating one or more symptoms of tricuspid regurgitation, by reducing the right heart size. One skilled in the art would further recognize that devices according to the present teachings could be used to treat various symptoms of mitral regurgitation. For example, the devices disclosed herein can be deployed against the left heart.

Various embodiments have been illustrated and described herein by way of examples, and one of ordinary skill in the art would recognize that variations can be made without departing from the spirit and scope of the present teachings. The present teachings are capable of other embodiments or of being practiced or carried out in various other ways. Also, it is to be understood that the phraseology and terminology employed herein is for the purpose of description and should not be regarded as limiting.

Unless otherwise defined, all technical and scientific terms used herein have the same meaning as commonly understood by one of ordinary skill in the art to which this present teachings belong. Methods and materials similar or equivalent to those described herein can be used in the practice or testing of the present teachings. In case of conflict, the patent specification, including definitions, will control. In addition, the materials, methods, and examples are illustrative only and not intended to be limiting.

We claim:

1. Apparatus comprising:
a delivery system comprising:
an access sheath, configured to be introduced to a treatment location outside a right side of a heart of a subject;
a delivery catheter; and
an inflation catheter; and
a device configured to be positioned at the treatment location, against the right side of the heart, the device comprising:
a tissue-binding adhesive;
a flexible outer layer encasing a primary cavity and a secondary cavity outside of the primary cavity, a portion of the flexible outer layer outside of the secondary cavity having a plurality of pores between the secondary cavity and the outside of the flexible outer layer;
a barrier separating the primary and secondary cavities, preventing moisture and gas from crossing the barrier; and
an injection port configured to allow an injection medium to be introduced into the primary cavity, the injection port comprising an injection tube that is disposed entirely within the primary cavity and is only in fluid communication with the primary cavity and not the secondary cavity, the injection port being configured for being detachably coupled to the inflation catheter,
wherein:
the device has a collapsed delivery profile and an inflated deployment profile,
in the collapsed delivery profile, the device is dimensioned to be advanced, within the access sheath, to the treatment location, while the secondary cavity contains the tissue-binding adhesive,
the device is inflatable into the inflated deployment profile by introducing the injection medium into the primary cavity via the inflation catheter and the injection port, and
introducing the injection medium into the primary cavity via the injection port squeezes the tissue-binding adhesive out of the secondary cavity via the pores.

2. The apparatus according to claim 1, wherein the barrier separating the primary and secondary cavities expands more than the portion of the flexible outer layer outside of the secondary cavity when the injection medium is introduced into the primary cavity, thereby allowing the primary cavity to expand at a greater rate than the secondary cavity, thereby causing expulsion of the tissue-binding adhesive through the pores.

3. The apparatus according to claim 1, wherein the device further includes a one-way valve disposed within the injection tube.

4. The apparatus according to claim 1, wherein the barrier extends longitudinally from a distal end to a proximal end of the device which is in the form of an inflatable balloon.

5. The apparatus according to claim 1, wherein the secondary cavity is disposed alongside the primary cavity.

6. The apparatus according to claim 1, wherein:
the portion of the flexible outer layer is a first portion of the flexible outer layer that delineates at least part of the primary cavity, and
a second portion of the flexible outer layer delineates at least part of the secondary cavity.

7. The apparatus according to claim 1, wherein the primary cavity is configured to inflate into a flat shape.

* * * * *